United States Patent [19]

Detty

[11] Patent Number: 5,472,413
[45] Date of Patent: Dec. 5, 1995

[54] UNIVERSAL FIT KNEE AND ELBOW BRACES WITH SPIDERS

[75] Inventor: Michael K. Detty, Tucson, Ariz.

[73] Assignee: Pro Orthopedic Devices, Inc., Tucson, Ariz.

[21] Appl. No.: 319,755

[22] Filed: Oct. 7, 1994

[51] Int. Cl.⁶ ............................................. A61F 5/00
[52] U.S. Cl. ...................... 602/26; 602/20; 602/23; 602/62; 2/62
[58] Field of Search .............................. 602/5, 20, 23, 602/26, 62; 2/62

[56] References Cited

U.S. PATENT DOCUMENTS

| | | |
|---|---|---|
| 3,318,305 | 5/1967 | Schultz . |
| 3,458,867 | 8/1969 | Moore et al. . |
| 3,463,147 | 8/1969 | Stubbs .................... 602/26 |
| 3,473,527 | 10/1969 | Spiro . |
| 3,804,084 | 4/1974 | Lehman . |
| 4,201,203 | 5/1980 | Applegate . |
| 4,287,885 | 9/1981 | Applegate . |
| 4,296,744 | 10/1981 | Palumbo . |
| 4,296,744 | 10/1981 | Palumbo ................. 602/26 |
| 4,378,009 | 3/1983 | Rowley et al. . |
| 4,693,241 | 9/1987 | Trznadel . |
| 4,765,318 | 8/1988 | Tranberg et al. ........... 602/26 |
| 5,024,216 | 6/1991 | Shiono .................. 602/26 |
| 5,069,457 | 12/1991 | Korzenowski . |
| 5,086,761 | 2/1992 | Ingram . |
| 5,168,577 | 12/1992 | Detty .................... 2/16 |
| 5,221,252 | 6/1993 | Caprio, Jr. et al. ....... 602/26 X |

OTHER PUBLICATIONS

Advertising Literature–1 Page Ingram–Performance Wrap–U.S. Pat. No. 5,086,761.

Primary Examiner—Richard J. Apley
Assistant Examiner—Kim M. Lee
Attorney, Agent, or Firm—Caesar, Rivise, Bernstein, Cohen & Pokotilow, Ltd.

[57] ABSTRACT

Knee and elbow braces arranged to fit all sizes of persons. Each brace is formed of a generally planar elastomeric, e.g., fabric-covered-neoprene, base member and a generally planar elastomeric, e.g., fabric-covered-neoprene, spider member attached to the base member. The base member includes two upper mounting straps, and two lower mounting straps to mount the brace on the person's joint. Each of the upper mounting straps is arranged to be wrapped in opposite directions around the limb above the joint to be protected. The lower mounting straps are arranged to be wrapped in opposite directions around the limb below the joint. The mounting straps include VELCRO® fasteners to hold the straps in place. When so wrapped the straps define cut away areas to prevent bunching of the material making up the brace when the joint is flexed. The spider member includes two upper and two lower tension straps which are arranged to be releasably secured by VELCRO® fasteners to respective ones of the mounting straps to effect the customized adjustment of tension provided by the brace to the joint. The spider member also provides cushioning and thermal insulation to the joint.

21 Claims, 5 Drawing Sheets

UNIVERSAL FIT KNEE AND ELBOW BRACES WITH SPIDERS

BACKGROUND OF THE INVENTION

This invention relates generally to knee and elbow braces and in particular to knee and elbow braces which are of the "one-size-fits-all" type, that is, they can fit a large range of sizes of limbs of persons wearing the brace.

Various types of knee and elbow braces are disclosed in the patent literature and are commercially available for helping to immobilize or support and stabilize the knee or elbow of persons to protect the joint against further injury and promote healing while allowing continuous use of the joint in sport or other activities. Examples of elbow braces in the patent literature are the following: U.S. Pat. No. 3,804,084 (Lehman) discloses a knee brace in the form of a planar pad arranged to be wrapped around the knee and having a central flap which utilizes a Velcro® fastener to extend about the brace in one direction to apply tension to the brace in that direction and a pair of upper and lower flaps which are fixed to the brace and are used to apply tension in the opposite direction. U.S. Pat. No. 4,296,744 (Palumbo) discloses a knee brace in the form of a sleeve having two straps which wrap around the brace to apply tension thereto in one direction above and below the knee and a central flap which wraps around the brace in the opposite direction to apply tension in that direction. Other patents disclosing various types of knee braces are U.S. Pat. Nos.: 3,318,305 (Schultz); 3,463,147 (Stubbs); 3,473,527 (Spiro); 4,201,203 (Applegate); 4,287,885 (Applegate); 4,693,241 (Trznadel); and 5,168,577 (Detty).

Elbow braces are also disclosed in the patent literature. For example, U.S. Pat. No. 5,069,457 (Korzenoski) discloses an elbow brace in the form of a sleeve having a tensioning strip secured to it. The brace is arranged to stiffen the elbow when swinging a golf club. U.S. Pat. No. 3,458,867 (Moore) discloses an elastic elbow protector in the form of a pad from which a pair of opposed straps expand to extend about the elbow.

While the aforementioned prior art knee and elbow braces may be generally suitable for their intended purposes, they nevertheless leave much to be desired from the standpoints of accommodating various sized limbs, and also supplying sufficient support to the joint to be braced. Thus, a need presently exists for knee and elbow braces which are of-the one-size-fits-all type and which have means to adjust and customize the support applied by the brace to provide good bracing support for various sized users.

OBJECTS OF THE INVENTION

Accordingly, it is the general object of the instant invention to provide knee and elbow braces which improve upon and overcome the shortcomings of existing braces.

It is a further object of the instant invention to provide knee and elbow braces, each of which can be applied to a wide range of sizes of joints and contiguous limbs.

It is a further object of the instant invention to provide one-size-fits-all knee and elbow braces, each of which can be readily applied to and removed from the joint, e.g., the knee or elbow to be protected.

It is yet a further object of the instant invention to provide knee and elbow braces wherein the amount of tension applied by each brace to prevent lateral or twisting movement of the joint is readily adjustable.

It is still yet a further object of the instant invention to provide knee and elbow braces, each of which includes a unitary base member for mounting the brace to the limb of the user over the joint and a unitary spider member secured to the base member for adjusting the amount tension applied by the brace to the joint.

It is still another object of the instant invention to provide knee and elbow braces, each of which wrap around the joint of the user in one direction above the joint and in the other direction below the joint.

It is still yet another object of the instant invention to provide knee and elbow braces, each of which wraps around the joint of the user above and below the joint with portions cut away to prevent bunching of the material making up the brace when the joint is flexed.

It is an additional object of the instant invention to provide knee and elbow braces, each of which provides added cushioning at the joint to protect the joint against further injury.

It is yet an additional object of the instant invention to provide knee and elbow braces, each of which provides added thermal insulation at the joint to maintain an elevated temperature at the joint.

SUMMARY OF THE INVENTION

These and other objects of the instant invention are achieved by providing a brace for a limb, e.g., knee or elbow, of a person. The brace basically comprises a base member and a spider member. The base member is formed of a generally planar sheet of elastomeric material, e.g., a fabric coated neoprene, and has a central portion, a pair of upper mounting straps secured to the central portion, and a pair of lower mounting straps secured to the central portion.

The central portion of the base member has a top edge and a bottom edge and a midline axis extending through the top and bottom edges. One of the pair of upper mounting straps extends in a first direction away from the midline axis adjacent the top edge, while the other of the pair of upper mounting straps extends in a second, opposite direction away from the midline axis adjacent the top edge. One of the pair of lower mounting straps extends in the first direction away from the midline axis adjacent the bottom edge, while the other of the pair of lower mounting straps extends in the second direction away from the midline axis adjacent the bottom edge.

Each of the upper mounting straps is arranged to be wrapped about a respective upper portion of the limb of the person and secured together by first upper releasable securement means, e.g., VELCRO® fasteners, irrespective of the size of the upper portion of the limb. Each of the lower straps is arranged to be wrapped about a respective lower portion of the limb and secured together by first lower releasable securement means, e.g., VELCRO® fasteners, irrespective of the size of the lower portion of the limb. This action effects the mounting of the brace on the person's limb over the joint to be braced.

The spider is formed of a generally planar sheet of elastomeric material, e.g., a fabric covered neoprene, and has a middle portion, a pair of upper tension straps secured to the middle portion, and a pair of lower tension straps secured to the middle portion. The middle portion of the spider member has an upper edge and a lower edge and a central axis extending through the upper and lower edges.

One of the pair of upper tension straps extends in a first direction away from the central axis of the spider member adjacent the upper edge, while the other of the pair of upper tension straps extends in a second, opposite direction away from the central axis of the spider member adjacent the upper edge. One of the pair of lower tension straps extends in the first direction away from the central axis of the spider member adjacent the lower edge, while the other of the pair of lower tension straps extends in the second direction away from the central axis adjacent the lower edge.

The middle portion of the spider member is fixedly secured to the central portion of the base member, with the axes of the base member and the spider member being co-linear.

Each of the upper tension straps is arranged to be wrapped about at least a respective upper mounting strap and secured thereto by second upper releasable securement means, e.g., VELCRO® fasteners, to apply a desired amount of tension to the brace above the joint, and each of the lower tension straps is arranged to be wrapped about at least a respective lower mounting strap and secured thereto by second lower releasable securement means, e.g., VELCRO® fasteners, to apply a desired amount of tension to the brace below the joint.

In both the knee and elbow braces at least the central and middle portions of the base member and spider member, respectively, are padded. In the knee brace the central and middle portions of the base member and spider member, respectively, include aligned openings to accommodate the patella of the person's knee.

In accordance with one aspect of the invention the double thickness of the brace formed by the overlapping central and middle portions of the base member and spider member, respectively, serves as additional padding or cushioning to protect the joint disposed thereunder. Moreover, the portions of the joint covered by the base member and the spider member will be maintained at a higher elevated temperature due to the thermal insulation qualities of the neoprene and the fact that those portions of the brace are of double thickness.

DESCRIPTION OF THE DRAWING

Other objects and many of the intended advantages of this invention will be readily appreciated when the same becomes better understood by reference to the following detailed description, when considered in connection with the accompanying drawing wherein.

DETAILED DESCRIPTION OF THE PREFERRED EMBODIMENTS

Referring now in greater detail to the various figures of the drawing, wherein like reference characters refer to like parts, there is shown in FIGS. 1–4 a knee brace 20 constructed in accordance with the present invention. The knee brace 20 basically comprises a base member 22 and a spider member 24. The base member can best be seen in FIG. 3 and basically comprises a unitary, planar sheet 26 (FIG. 3) of an elastomeric material cut into a predetermined shape, to be described later. The material is preferably a fabric-coated neoprene, with the fabric 28 being secured to the outer surface of the neoprene sheet. The neoprene is of a substantial thickness, e.g. approximately 4 mm. thick, to provide cushioning. In accordance with the preferred aspect of the invention, the fabrics 28 is tufted or plush so that it can act as the multiple loop fastening component of a Velcro® fastening system. This feature facilitates the mounting of the brace on the knee of the wearer as will be described later.

Figures 1, 3:
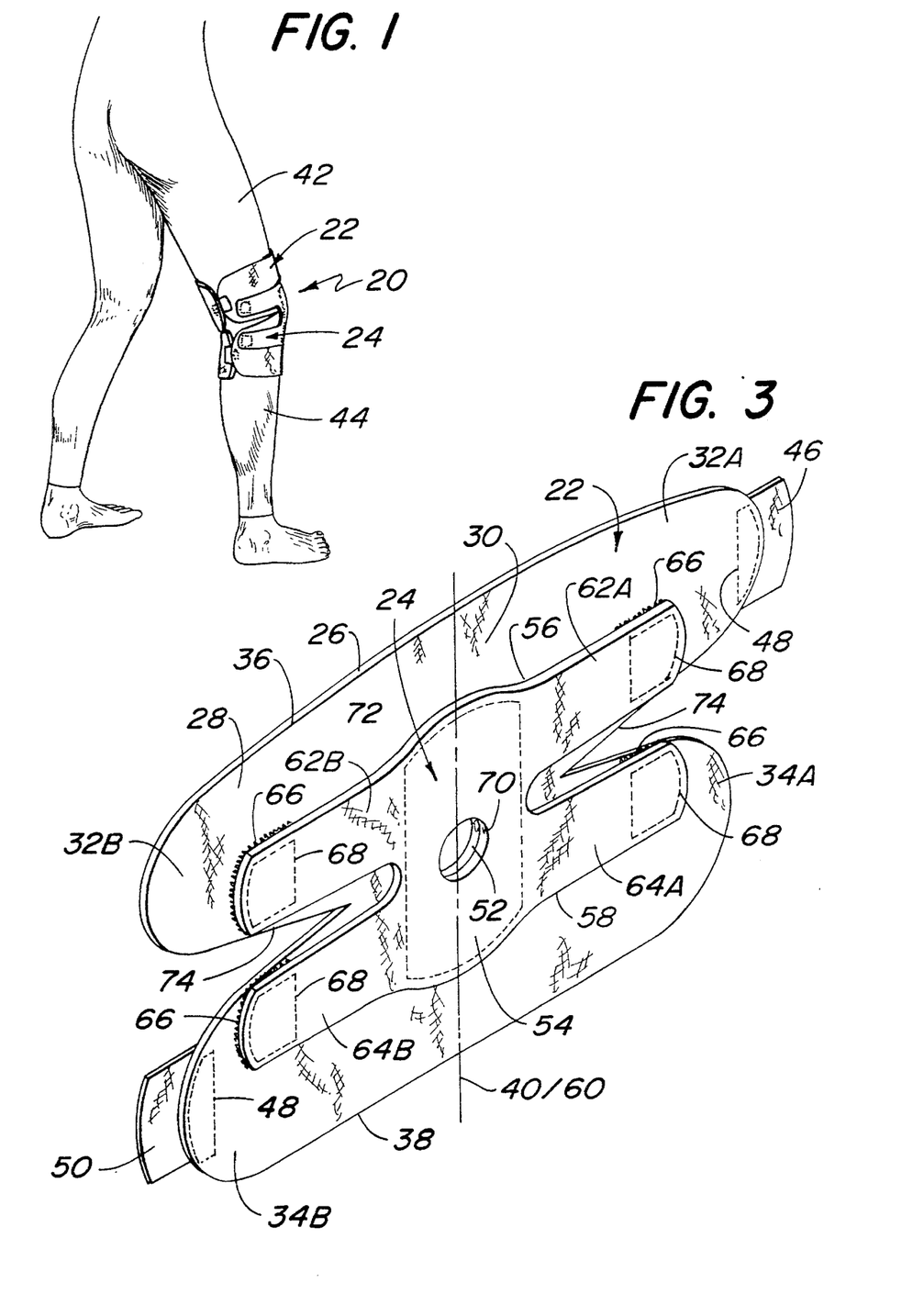
FIG. 1 is an isometric view of a knee brace constructed in accordance with this invention mounted on the leg of a person to protect and stabilize the person's knee.
FIG. 3 is a reduced isometric view of the knee brace shown in FIG. 3 prior to application to the person's knee.

As can be seen clearly in FIG. 3 the base member 22 includes a central portion 30, a first upper mounting strap 32A, a second upper mounting strap 32B, a first lower mounting strap 34A, and a second lower mounting strap 34B. The straps project from respective portions of the central portions of the base member. The central portion of the base member includes an upper edge 36, a lower edge 38, and a mid-line axis 40 extending through the central portion 30 of the base member through the upper and lower edges 36 and 38, respectively. The upper straps 32A and 32B are each arranged to be bent or wrapped about a respective portion of a upper leg 42 (FIG. 1) of the person immediately over the knee so that the mid-portion 30 of the base member 22 is disposed over the anterior portion of the leg above the knee. In a similar manner each of the lower mounting straps 34A and 34B is arranged to be bent or wrapped around the wearer's lower leg 44 immediately below the knee, all as shown in FIG. 1. The upper mounting strap 32A includes a tab 46 of a multi-hook Velcro® fastener secured to the inner surface of the free end thereof by plural stitches 48. The lower mounting strap 34B includes a similar multi-hook Velcro® tab 50 secured to the inner surface of the free end thereof by plural stitches 48. As should be appreciated, the Velcro® tab 46 of the upper mounting strap 32A extends in the opposite direction with respect to axis 40 to the Velcro® tab 50 of the lower mounting strap 34B. The reason for this tab arrangement is that the brace is designed so that the upper mounting strap 32A is to be wrapped around the leg over the upper mounting strap 32B so that the hooks of the tab 46 extend over the fabric surface 28 of the mounting strap 32B to enable the tab to be releasably secured to the multiple loops forming the plush fabric coating of the strap 32B. The amount of overlap is adjustable to accommodate any size of upper leg 42 so that the strap 32A and 32B encircle the leg to hold the brace in place thereon, and to adjust the amount of tension in the straps. The lower mounting strap 34B having the Velcro® tab 50 thereon is arranged to be wrapped about the lower limb 44 over the outer surface of the lower mounting strap 34A in a similar manner, albeit from the opposite direction. This mounts the lower portion of the base on the lower limb.

Since the direction of wrapping the upper mounting straps and the lower mounting straps are in opposite directions the tension provided by the mounting of the brace on the leg is equalized on the knee.

As can be seen clearly in FIG. 3, the center of the central portion 30 of the base member 22 includes an opening or a hole 52 therein. This hole is provided to accommodate the patella of the knee, when the brace is in place on the leg.

The spider member 24 serves various functions, namely, it enables the user to customize tension to be applied to the brace at desired portions thereof, while also providing additional cushioning for the joint, e.g., knee to be protected, and in addition, provides an additional thermally insulative layer to the brace to maintain the knee at an elevated temperature when the brace is in place.

In accordance with a preferred embodiment the spider member is fixedly secured to the central portion 30 of the base member (as will be described later).

The shape of the spider member is somewhat similar to the base member, albeit, somewhat smaller in size. To that end, the spider member includes a middle portion 54 having an upper edge 56, a lower edge 58, and a center line 60 extending therethrough. A pair of upper tensioning straps 62A and 62B extend from the central portion of the spider member adjacent to the top edge 56 thereof in opposite directions from the center line 60 of the spider member. In a similar manner, a pair of lower tensioning straps 64A and 64B extend from the central portion of the spider member adjacent to the lower edge 58 thereof on opposite sides of the center line.

In accordance with the preferred embodiment of the invention, the spider member 24 is formed of the same material as that making up the base member 22. The free end of each of the tensioning straps 62A, 62B, 64A, and 64B of the spider includes respective multi-hook Velcro® patches 66 mounted on the inner surface thereof by stitches 68. The central or middle portion 54 of the spider includes a hole or opening 70 which is co-extensive in size with the hole in the middle portion of the base member. The spider member is fixedly secured to the base member by plural lines of stitches 72 with the midline axis 40 of the base member co-linear with the central axis 60 of the spider member, whereupon the two openings 52 and 70 are aligned.

The material making up the spider member 24 is preferably of the same thickness as that of the base member 22. Thus, the double thickness of the brace 20 where the central portion 30 of the base member and the middle portion 54 of the spider member 24 are secured together provides additional cushioning or padding to the knee when the brace is in place. Moreover, the double thickness of the brace at the central and middle portions, coupled with the thermally insulative properties of neoprene, insures that when the brace is worn over the knee, heat will be retained under the brace thereby keeping the knee at an elevated temperature. This elevated temperature can facilitate healing of an injury or prevent the exacerbation thereof.

Figure 2:
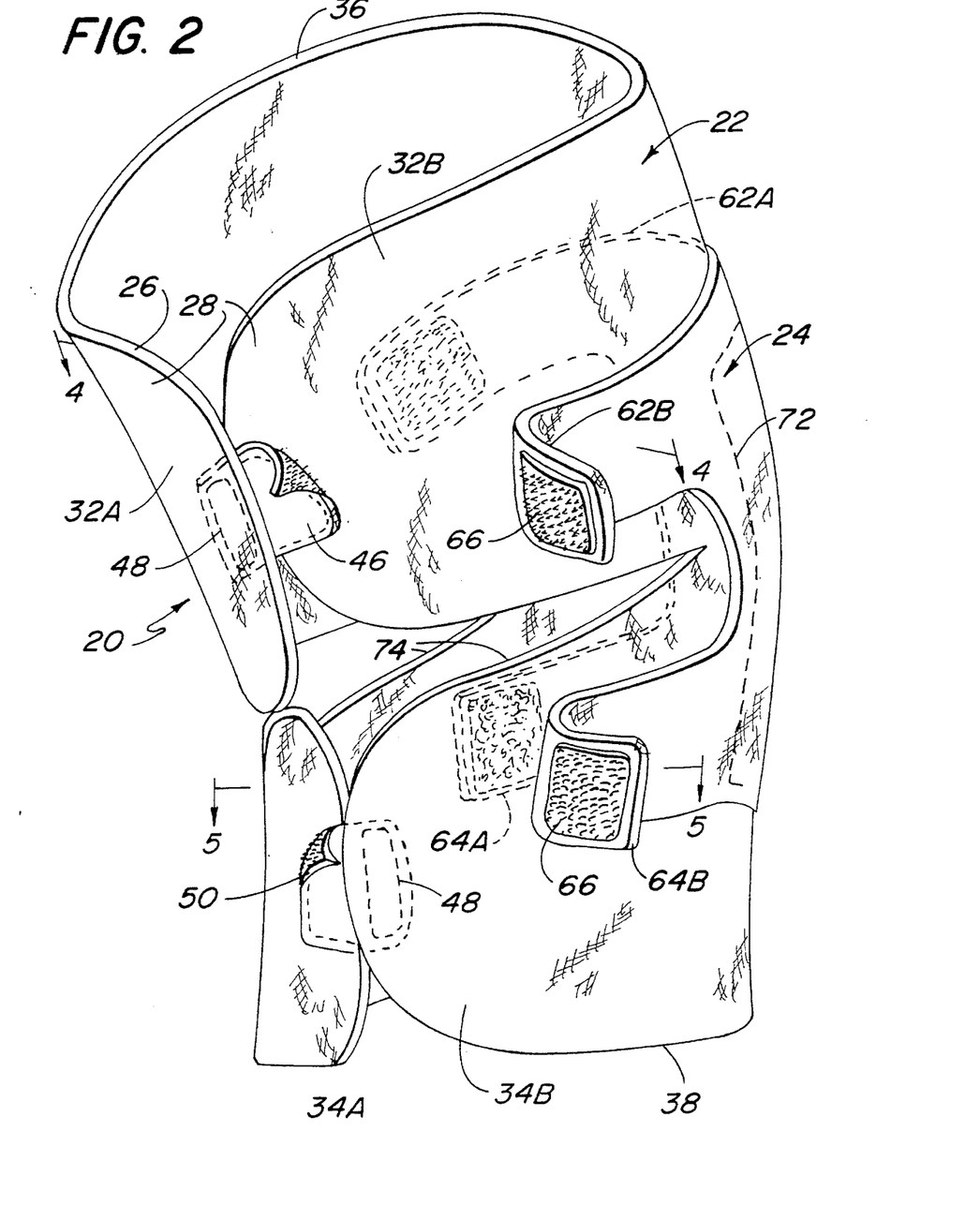
FIG. 2 is an enlarged isometric view of the knee brace of FIG. 1 showing the attachment of the upper and lower mounting straps of the base member of the brace about the leg of the user and the attachment of the upper and lower tension straps of the spider member to the respective mounting straps of the base member to apply the desired tension to the brace.
Figure 4:
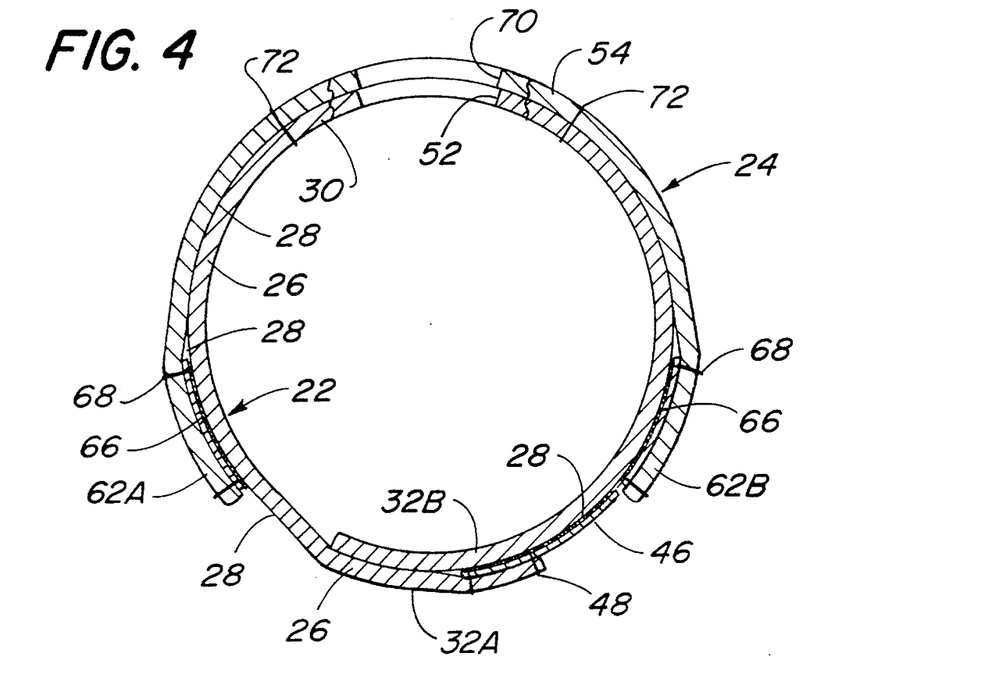
FIG. 4 is a sectional view of the knee brace taken along the line 4—4 of FIG. 2.
Figure 5:
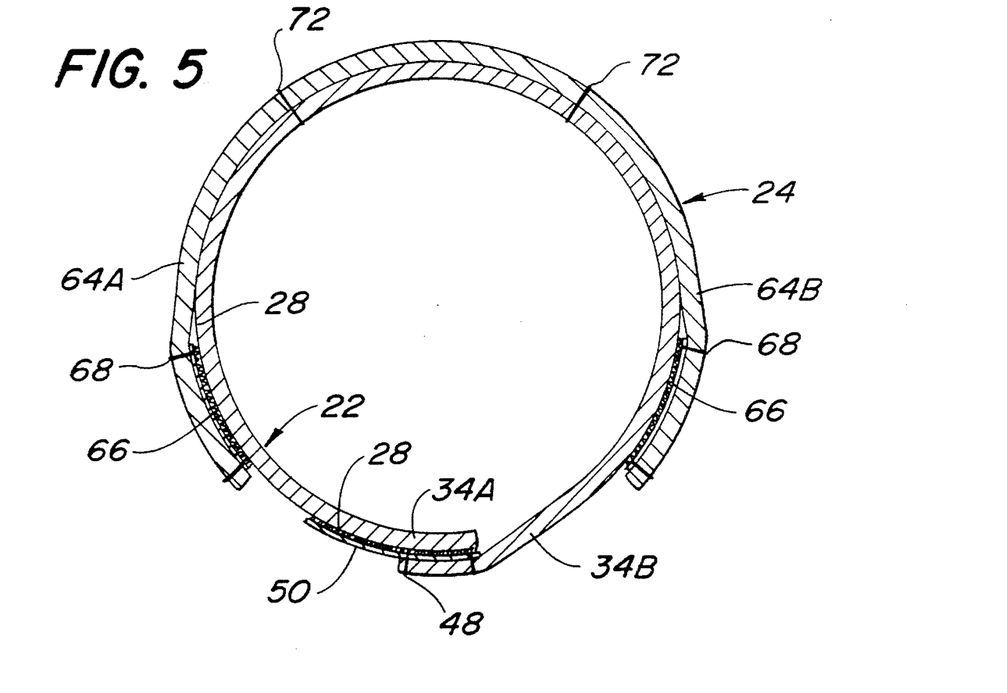
FIG. 5 is a sectional view of the knee brace taken along the line 5—5 of FIG. 2.

Referring now to FIGS. 2, 4 and 5, the mounting of the brace on the leg of a person will now be described. The brace is initially oriented like that shown in FIG. 3 so that it is generally planar. The brace is then held against the anterior portion of the upper limb 42 so that the upper portion of the middle of the base member is over the knee. The mounting strap 32B is then wrapped around the posterior portion of the upper leg to whatever degree of tension is desired. The opposite mounting strap 32B having the Velcro® attachment tab secured thereto is then wrapped around the upper leg so that the tab is disposed over the outer fabric surface 28 of the mounting strap 32B. The amount of overlap and tension applied to the upper mounting strap is adjustable to whatever the wearer desires. Once the tab is disposed over the fabric covering on the opposite mounting strap, the multiple hook elements of the tab will engage the plush fabric to releasably secure the upper mounting strap 32A over and to the upper mounting strap 32B. Inasmuch as the material making up the base member is elastomeric, the mounting straps can stretch, thereby enabling the upper mounting straps to encircle the upper leg of any size wearer.

The lower mounting straps 34A and 34B are then secured about the lower leg below the knee in a similar manner. To that end, the lower mounting strap 34A is pulled or wrapped about the anterior portion of the lower leg 42 below the knee and held in place while the opposite lower mounting strap 34B having the Velcro® mounting tab 50 thereon is pulled and wrapped around the opposite portion of the lower leg and the tab 50 brought into engagement with the fabric of the lower mounting strap 34A to thereby releasably secure the multiple hook-like elements of the tab to the fabric. At this time, the brace is fully mounted on the wearer's knee.

Additional tension can now be provided to the brace by the stretching selected ones or all of the tensioning straps 62A, 62B, 64A, and 64B about respective portions of the mounting straps of the base member and the securement of those tensioning straps thereto. This can be readily accomplished since the outer surface 28 of the base member is entirely covered with the plush fabric so that the Velcro® patches 66 can be releasably secured thereto when they engage that surface.

As will be appreciated by those skilled in the art, each of the tensioning straps can be extended or stretched to any position and location within its range of movement. Thus, the upper tension strap 64A can be stretched over its associated upper mounting strap 32A and secured thereto at any point thereon. Moreover, the upper tension strap 64A may even be stretched so that it extends over the other mounting strap 32B for securement to the outer surface thereof. In a similar manner the tension strap 62B may be stretched to be secured to the associated mounting strap 32B or may be stretched further so that it extends to the opposite upper mounting strap 32A for securement thereto. The lower tension straps can be similarly adjusted. Moreover, the tension straps may be oriented so that when they are secured to the mounting straps of the base member they do not extend perpendicularly to the co-linear axes 40 and 70. This feature enables the tension straps to be secured to the mounting straps at various positions, whereupon the user can customize the amount of tension and the direction of tension which is applied to the knee by spider member. This enables user to customize the support and stabilization provided by the brace to his/her desires or needs, irrespective of the size of the joint being braced.

As can be seen clearly in FIGS. 2 and 3 a V-shaped recess 74 exists between the upper mounting strap 32A and the lower mounting strap 34A and a similar V-shaped recess 74 exists between the upper mounting strap 32B and the lower mounting strap 34B. Accordingly, when the brace 20 of the subject invention is mounted on the knee the two V-shaped recesses 74 define cutaway areas at the posterior portion of the leg at the knee, to thereby prevent bunching up of the material making up the brace when the knee is flexed. This ensures that the brace can be worn comfortably.

Figure 6:
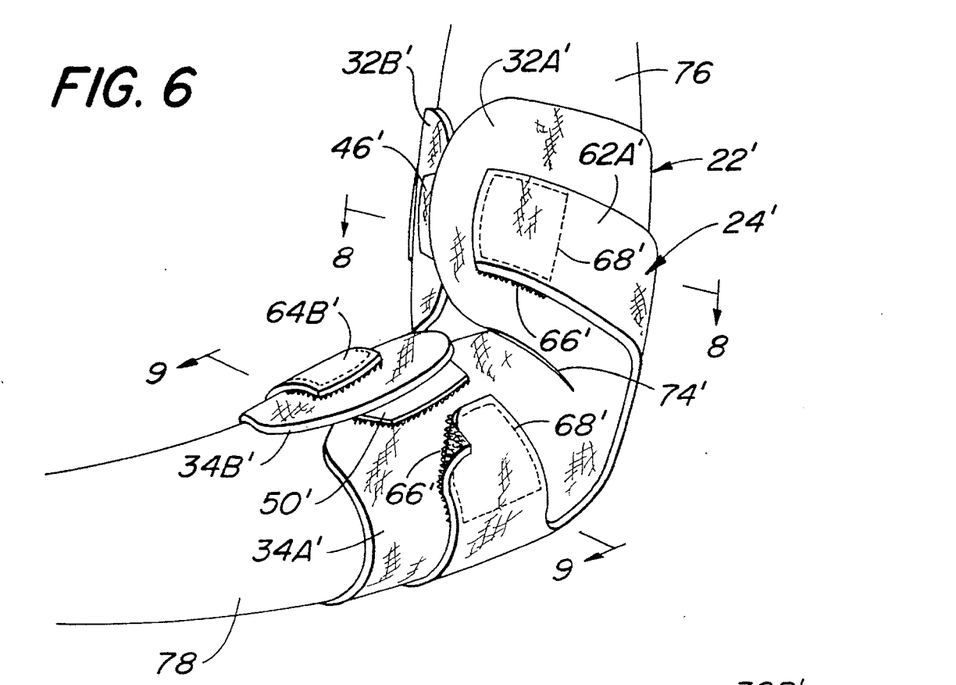
FIG. 6 is an isometric view of an elbow brace constructed in accordance with this invention shown mounted on the elbow of a person.
Figure 7:
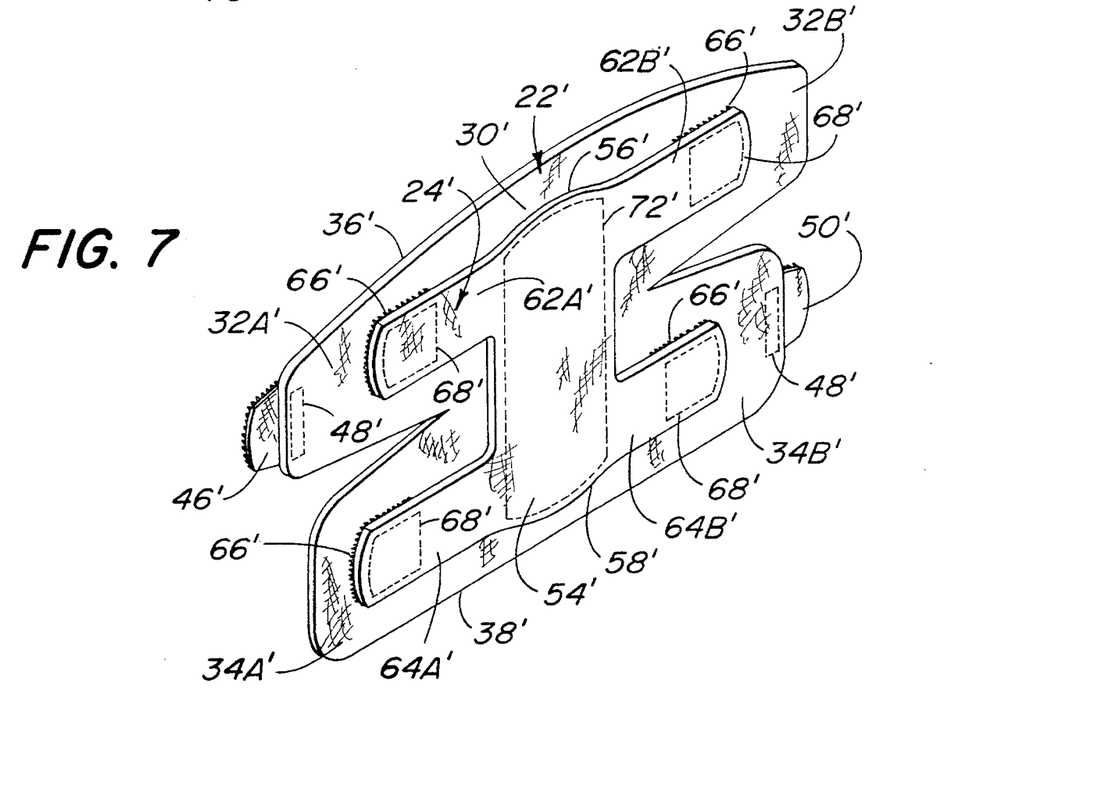
FIG. 7 is an isometric view of the elbow brace shown in FIG. 6 prior to application to the person's elbow.
Figure 8:
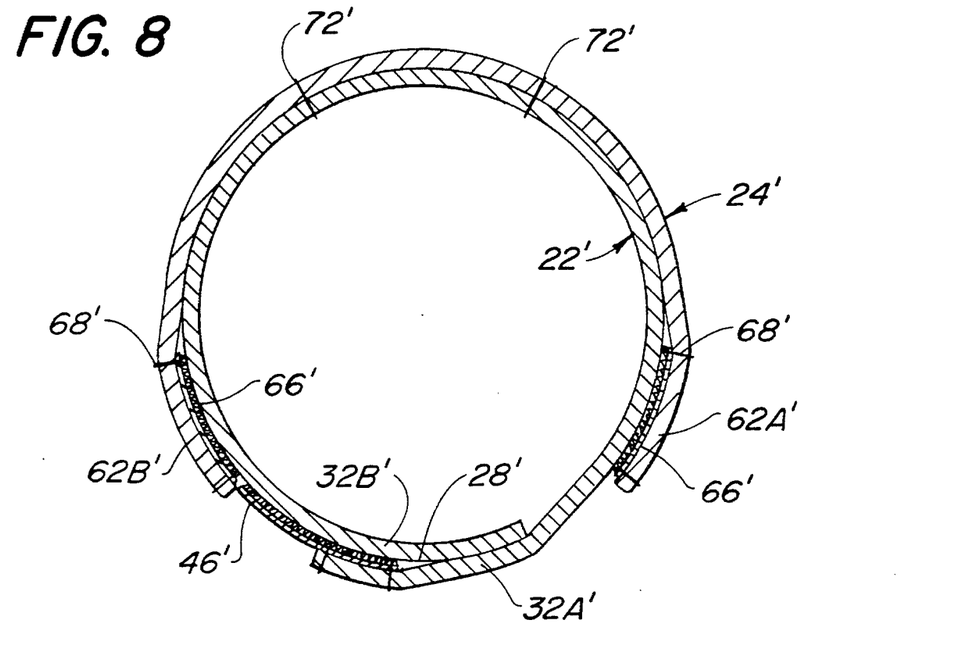
FIG. 8 is a sectional view of the elbow brace taken along the line 8—8 of FIG. 6.
Figure 9:
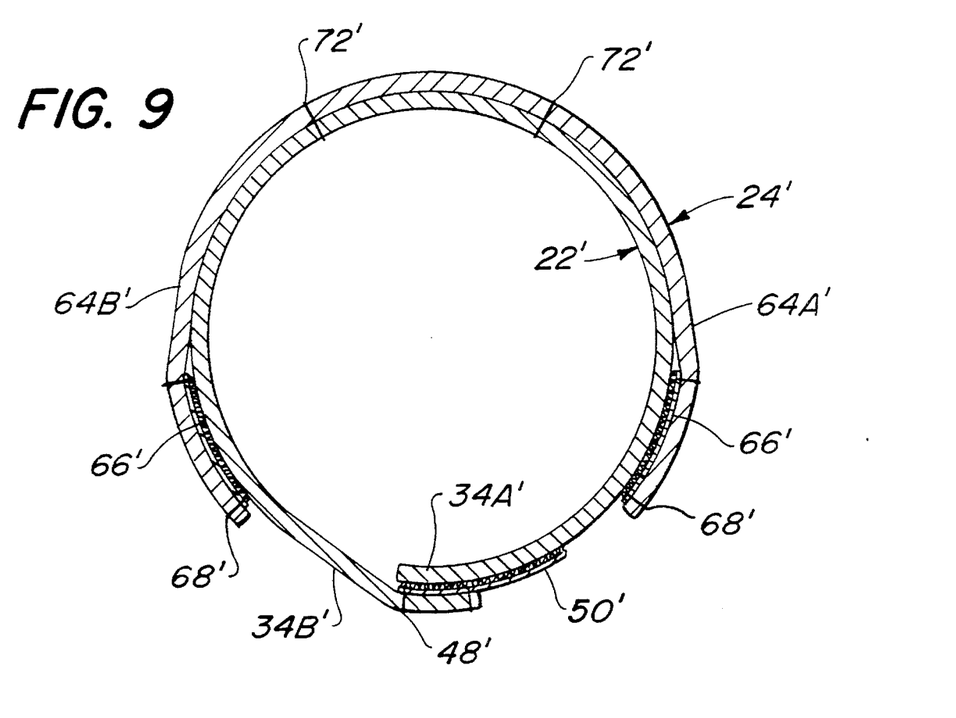
FIG. 9 is a sectional view of the elbow brace taken along the line 9—9 of FIG. 6.

In FIG. 6 there is shown an elbow brace 100 constructed in accordance with the subject invention. As can be seen by reference to FIG. 7 the elbow brace is very similar in construction to the knee brace, as described heretofore except for the specific shape of the base member and the spider member and the size thereof. Thus, all the corresponding components of the elbow brace 100 which correspond to the components of the knee brace 20 will be given the same reference number as the knee brace followed by a "prime" suffix. Moreover, the common structural features and common operation of the elbow brace will not be reiterated in the interest of brevity. Thus, as can be seen in FIG. 7 the elbow brace 100 includes a base member 22' and a spider member 24', each of which is constructed similarly to the corresponding base and spider members 22 and 24 of the knee brace 20, except for the fact that neither the base member nor the spider member includes a central opening therein and that the spider member 24' is more "H-shaped" that the spider member 24.

The elbow brace is applied to the elbow joint in a similar manner to that described heretofore. Thus, as can be seen in FIG. 6, the base member 22' is applied over the elbow so that the central portion 30' of the base member is approximately centered over the elbow. The upper mounting strap 32B' is then wrapped around the person's upper arm 76 to the desired degree of tension, whereupon the opposed upper mounting strap 32B having the Velcro® securement tab 46' at the free end thereof is stretched to the desired tension over the upper mounting strap 34B' and the hooks of the tab 46 are brought into engagement with the outer plush surface thereof to secure the straps together. The lower mounting strap 34A' is then stretched around the person's forearm 78 to the desired degree of tension and is held in place. Then the opposed mounting strap 34B' having the Velcro® tab 50' secured thereto is stretched to the desired degree of tension and the tab secured to the outer plush surface of the underlying mounting strap 34A' to secure the two mounting straps together. The tension straps 62A', 62B', 64A' and 64B' are then stretched and pulled over their associated mounting straps to secure them in the desired positions to apply the desired amount of tension to the brace in a similar manner as described heretofore.

It should be pointed out at this junction that other materials, than those described heretofore, can be used to make the braces of this invention. For example, neoprene having a tufted fabric covering may not be used, i.e., the neoprene may not be covered by any fabric or may be covered by a non-tufted fabric, such as smooth nylon. In the case where the material of the base member does not include a plush fabric covering, the outer surface of the base member should include at least patches of a plush or multi-loop VELCRO® component secured thereto for engagement by the multi-hook VELCRO® component of the tabs of the mounting straps and the patches of the tension straps to enable those straps to be secured thereto at various positions thereon. In fact, other releasably securable means can be used in lieu of VELCRO® components, if desired. Moreover, in some cases, it may not be desired to use neoprene as the material of the base member and/or the spider member. Thus, other elastic materials, with or without cushioning and thermal retention properties may be used, for either, if desired. Further still, the base member and the spider member need not be unitary members, i.e., formed of a single piece of material. Thus, the base member may be formed of plural pieces which are secured together to form an integral assembly. The spider may be similarly constructed.

As should be appreciated from the foregoing, the braces of the subject invention can be applied to various sized limbs, thereby providing true "one-size-fits-all" braces. Moreover, the tension straps of the spider provide customized tensioning of the brace at any area desired by the user. The double thickness of the brace at its front portion provides additional cushioning as well as thermal retention properties for the brace. Moreover, the opposite direction wrapping of the upper mounting straps to the lower mounting straps provides increased balance and stability for the brace, as compared to prior art braces which include upper and lower portions wrapped in the same direction. Moreover, with the subject brace mounted in place and the tension straps as adjusted greater resistance of the brace to transverse or twisting stress can be achieved than with the prior art elastic braces.

Further still, the application of the brace to the joint can be achieved quite easily and simply and does not require complicated wrappings of long straps. All that is required is to pull and stretch the various mounting straps and secure the Velcro® fastening means. The application of customized tension to the brace is also readily achieved by stretching and fastening the tension straps to the desired area of the mounted brace.

Not only is are subject knee and elbow braces true one-size-fits-all devices which can be readily applied and adjusted to provide the desired stabilization and support, their constructions are very simple. In this regard each can be readily fabricated from a sheet of fabric covered neoprene. Once fabricated and assembled, the generally flat shape of each brace enables it to be transported and warehoused inexpensively, as compared to the prior art.

Without further elaboration, the foregoing will so fully illustrate my invention, that others may, by applying current or future knowledge, readily adapt the same for use under the various conditions of service.

I claim:

1. A brace for a limb of a person, the limb having an upper portion, a lower portion, and a flexible joint therebetween, said brace comprising an unitary base member and an unitary spider member, said base member being formed of a generally planar sheet of elastomeric material and having a central portion, a pair of upper mounting straps secured to said central portion of said base member, and a pair of lower mounting straps secured to said central portion of said base member, said central portion of said base member having a top edge and a bottom edge and having a midline axis extending through said top and bottom edges, a first one of said pair of upper mounting straps extending in a first direction away from said midline axis adjacent said top edge, a second one of said pair of upper mounting straps extending in a second, opposite direction away from said midline axis adjacent said top edge, a first one of said pair of lower mounting straps extending in said first direction away from said midline axis adjacent said bottom edge, a second one of said pair of lower mounting straps extending in said second direction away from said midline axis adjacent said bottom edge, each of said upper mounting straps being arranged to be wrapped about a respective upper portion of the limb with said first upper strap being disposed over said second upper strap for releasable securement thereto by first upper releasable securement means irrespective of the size of the upper portion of the limb, each of said lower straps being arranged to be wrapped about a respective lower portion of the limb with said second lower strap being disposed over said first lower strap for releasable securement thereto together by first lower releasable securement means irrespective of the size of the lower portion of the limb, whereupon said brace is mounted on the limb, said spider being formed of a generally planar sheet of elastomeric material and having a middle portion, a pair of upper tension straps secured to said middle portion, and a pair of lower tension straps secured to said middle portion, said middle portion having an upper edge and a lower edge and a central axis extending through said upper and lower edges, a first one of said pair of upper tension straps extending in said first direction away from said central axis adjacent said upper edge, a second one of said pair of upper tension straps extending in said second direction away from said central axis adjacent said upper edge, a first one of said pair of lower tension straps extending in said first direction away from said central axis adjacent said lower edge, a second one of said pair of lower tension straps extending in said second direction away from said central axis adjacent said lower edge, said middle portion of said spider member being fixedly secured to said central portion of said base member with said midline and central axes being co-linear, each of said upper tension straps being arranged to be wrapped about at least a respective upper mounting strap and secured thereto at various positions thereon by second upper releasable securement means to apply a desired amount of tension to the brace above the joint, and each of said lower tension straps being arranged to be wrapped about at least a respective lower mounting strap and secured thereto at various positions thereon by second lower releasable securement means to apply a desired amount of tension to the brace below the joint.

2. The brace of claim 1 wherein said brace comprises a knee brace, with the joint being the knee, and wherein said central portion of said base member and said middle portion of said spider member are padded and each includes an opening therein, with said openings being aligned with each other to accommodate the patella of the knee of the person therein.

3. The brace of claim 1 wherein said elastomeric material comprises neoprene.

4. The brace of claim 1 wherein said neoprene is covered by a fabric.

5. The brace of claim 1 wherein said releasable securement means comprise VELCRO® means.

6. The brace of claim 1 wherein said first upper securement means comprises a patch of a multi-hook component secured to said first upper mounting strap and a fabric portion on said second upper mounting strap to which said multi-hook component may be releasably secured, and wherein said first lower securement means comprises a patch of a multi-hook component secured to said second lower mounting strap and a fabric portion on said first lower mounting strap to which said multi-hook component may be releasably secured.

7. The brace of claim 6 wherein said base member comprises an outer surface and wherein said entire outer surface forms said fabric portion.

8. The brace of claim 1 wherein said base member comprises a fabric outer surface, wherein said spider member comprises a inner surface, and wherein said second upper releasable securement means comprises a patch of a multi-hook component secured to the inner surface each of said tension straps for releasable securement to the fabric outer surface of said base member.

9. The brace of claim 6 wherein said base member comprises a fabric outer surface, wherein said spider member comprises a inner surface, and wherein said second upper releasable securement means comprises a patch of a multi-hook component secured to the inner surface each of said tension straps for releasable securement to the fabric outer surface of said base member.

10. The brace of claim 1 wherein said brace comprises an elbow brace, with the joint being the elbow, and wherein said central portion of said base member and said middle portion of said spider member are padded.

11. The brace of claim 14 wherein said releasable securement means comprise VELCRO® means.

12. The brace of claim 11 wherein said first upper securement means comprises a patch of a multi-hook component secured to said first upper mounting strap and a fabric portion on said second upper mounting strap to which said multi-hook component may be releasably secured, and wherein said first lower securement means comprises a patch of a multi-hook component secured to said second lower mounting strap and a fabric portion on said first lower mounting strap to which said multi-hook component may be releasably secured.

13. The brace of claim 12 wherein said base member comprises an outer surface and wherein said entire outer surface forms said fabric portion.

14. A brace for a limb of a person, the limb having an upper portion, a lower portion, and a flexible joint therebetween, said brace comprising: an unitary base member and an unitary spider member, said base member having a longitudinal midline axis and being formed of an elastomeric material having a pair of upper mounting straps and a pair of lower mounting straps, said upper mounting straps comprising first and second straps, said first upper mounting strap extending in a first direction from said midline axis and said second upper mounting strap extending in a second and opposite direction from said midline axis, said upper mounting straps being arranged to be wrapped about the upper portion of the limb, with said first upper mounting strap overlying said second upper mounting strap and being releasably securable thereto at various points thereon, said lower mounting straps comprising first and second straps, said first lower mounting strap extending in said first direction and said second lower mounting strap extending in said second direction, said lower mounting straps being arranged to be wrapped about the lower portion of the limb, with said second lower mounting strap overlying said first lower mounting strap and being releasably securable thereto at various points thereon, said spider member being secured over said base member and comprising an elastomeric material having stretchable tension straps to be releasably secured to said mounting straps of said base member at various points thereon to adjust the tension applied by the brace to the joint.

15. The brace of claim 14 wherein said spider member comprises central portion, a pair of upper tension straps and a pair of lower tension straps, said central portion having a central axis, with one of said pair of upper tension straps extending in a first direction away from said central axis and the other of said pair of upper tension straps extending in a second, opposite direction away from said central axis, with one of said pair of lower tension straps extending in said first direction away from said central axis and with the other of said pair of lower tension straps extending in said second direction away from said central axis.

16. The brace of claim 15 wherein said base member includes a central portion having a midline axis from which said mounting straps project, and wherein said spider member includes a middle portion from which said tension straps project, said spider member being secured to said base member so that said midline axis and said central axis are co-linear, each of said upper tension straps being arranged to be wrapped about at least a respective upper mounting strap and releasably secured thereto at various points thereon by securement means to apply a desired amount of tension to the brace above the joint, and each of said lower tension straps being arranged to be wrapped about at least a respective lower mounting strap and secured thereto by releasable securement means to apply a desired amount of tension to the brace below the joint.

17. The brace of claim 16 wherein said brace comprises a knee brace, with the joint being the knee, and wherein said central portion of said base member and said middle portion of said spider member are padded and each includes an opening therein, with said openings being aligned with each other to overlie and accommodate the patella of the knee of the person therein.

18. The brace of claim 16 wherein said brace comprises an elbow brace, with the joint being the elbow, and wherein said central portion of said base member and said middle portion of said spider member are padded to overlie the elbow.

19. The brace of claim 14 wherein a pair of recesses are located between said upper mounting straps and said lower mounting straps to prevent bunching of the material forming the brace when the brace is in place on the joint and the joint is flexed.

20. The brace of claim 14 wherein said elastomeric material comprises neoprene.

21. The brace of claim 1 wherein said releasable securement of said mounting straps together is by use of multi-hook and multi-loop fastening means.

* * * * *